United States Patent
Struemper

(10) Patent No.: US 12,042,136 B2
(45) Date of Patent: Jul. 23, 2024

(54) TREATMENT OF A RUPTURE OF A BODY COMPONENT

(71) Applicant: Rudolf Struemper, Cologne (DE)

(72) Inventor: Rudolf Struemper, Cologne (DE)

( * ) Notice: Subject to any disclaimer, the term of this patent is extended or adjusted under 35 U.S.C. 154(b) by 833 days.

(21) Appl. No.: 15/666,702

(22) Filed: Aug. 2, 2017

(65) Prior Publication Data

US 2018/0256143 A1  Sep. 13, 2018

(51) Int. Cl.
*A61B 17/00* (2006.01)
*A61B 17/56* (2006.01)
*A61B 34/20* (2016.01)
*A61B 90/00* (2016.01)
*A61L 24/10* (2006.01)

(52) U.S. Cl.
CPC .. *A61B 17/00491* (2013.01); *A61B 17/00234* (2013.01); *A61B 17/56* (2013.01); *A61B 34/20* (2016.02); *A61B 90/39* (2016.02); *A61L 24/106* (2013.01); *A61B 2017/00495* (2013.01); *A61B 2017/564* (2013.01); *A61B 2017/567* (2013.01); *A61B 2034/2051* (2016.02); *A61B 2090/3954* (2016.02); *A61B 2090/3966* (2016.02); *A61L 2400/06* (2013.01)

(58) Field of Classification Search
CPC ... A61B 17/00491; A61B 34/20; A61B 90/39; A61B 17/00234; A61B 17/56; A61B 2034/2051; A61B 2090/3954; A61B 2090/3966; A61B 2017/00495; A61B 2017/564; A61B 2017/567; A61L 24/106; A61L 2400/06
See application file for complete search history.

(56) References Cited

U.S. PATENT DOCUMENTS

| | | | |
|---|---|---|---|
| 5,962,405 A * | 10/1999 | Seelich | A61L 24/106 514/13.6 |
| 8,403,923 B2 * | 3/2013 | Whitlock | A61L 27/50 606/27 |
| 2002/0077588 A1 * | 6/2002 | Schneider | A61M 5/007 604/82 |

FOREIGN PATENT DOCUMENTS

WO  WO-2015188040 A2 * 12/2015 ............. A61K 47/32

OTHER PUBLICATIONS

Ishimura et al, Arthroscopic Meniscal Repair Using Fibrin Glue. Part II: Clinical Applications, Arthroscopy: The Journal of Arthroscopic and Related Surgery, 1997, 13, pp. 558-563.*
Arthroscopy Meniscal Surgery, from https://scottasigmanmd.com/knee/arthroscopy-meniscal-surgery/, pp. 1-2, accessed Nov. 19, 2018.*
Tisseel, from Baxter Healthcare Corporation, pp. 1-8, 2013.*
Ward et al, Basic Knee Arthroscopy Part 2: Surface Anatomy and Portal Placement, Arthroscopy Techniques, 2013, 2, pp. e501-e502.*
Lefevre et al, A Current Review of the Meniscus Imaging: Proposition of a Useful Tool for Its Radiologic Analysis, Radiology Research and Practice, 2016, pp. 1-25.*
Hufner et al, Utility of Intraoperative Three-Dimensional Imaging at the Hip and Knee Joints with and without Navigation, J Bone Joint Surg Am., 2009, 91, pp. 33-42.*
Schirmer et al, Signa SP/2—A MRI System for Image Guided Surgery, Med. Laser Appl., 2002, 17, pp. 105-116.*
Kettenbach et al, Interventional and intraoperative magnietic resonance imaging, Annu. Rev. Biomed. Eng., 2000, pp. 661-690.*
Ovcacikova, Special ceramic materials, from https://pdfs.semanticscholar.org/ba50/ece245144abf9062372f3ff1a49db218df80.pdf, Feb. 19, 2020, pp. 1-43.*
Eggers et al, Image-to-patient registration techniques in head surgery, Int. J. Oral Maxillofac. Surg., 2006, 35, pp. 1081-1095.*

* cited by examiner

*Primary Examiner* — Li N Komatsu
(74) *Attorney, Agent, or Firm* — Occhiuti & Rohlicek LLP

(57) ABSTRACT

A fibrin adhesive for use in the minimally-invasive treatment of a rupture of a body component formed by hard connective tissue adhesively bonds to that body component. A suitable treatment method features locating the rupture, providing the fibrin adhesive, and supplying the fibrin adhesive at the body component to be treated.

15 Claims, 1 Drawing Sheet

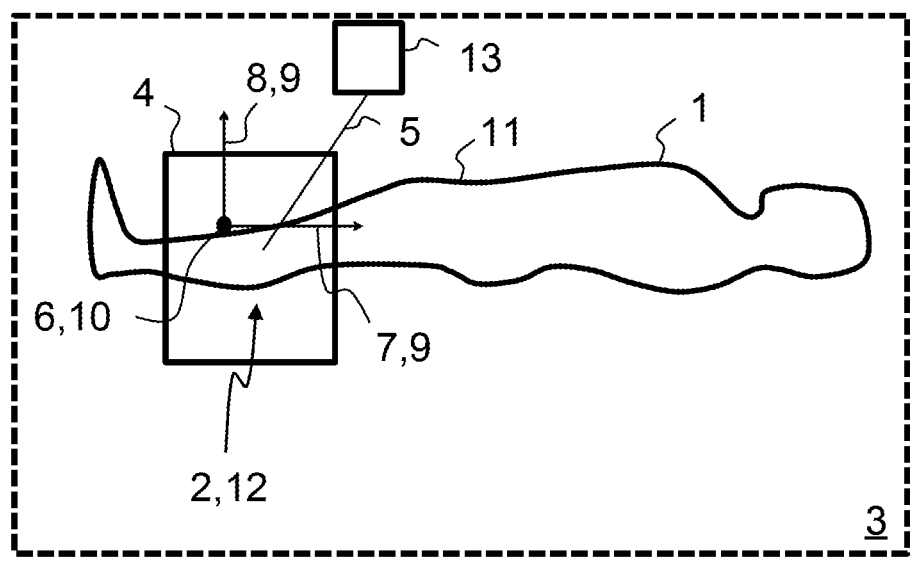

TREATMENT OF A RUPTURE OF A BODY COMPONENT

RELATED APPLICATION

This application claims the benefit of German Application No. 102017105256.9 priority date of Mar. 13, 2017, the contents of which are herein incorporated by reference.

FIELD OF INVENTION

The invention relates to the treatment of a ruptured or torn body component, and in particular, to a ruptured or torn body component that is formed from hard connective tissue.

BACKGROUND

Certain body components are formed substantially from hard connective tissue. Examples include tendons, cartilage, menisci, and capsules. Ruptures regularly occur in such body components.

In the event of a rupture, the ruptured body part is entirely or partially torn. Such a rupture is often painful. It can also impair the patient's freedom of movement. Treatment of a rupture is therefore often desirable.

A particularly common injury is a torn meniscus in the knee. Known methods of treating a torn meniscus include arthroscopically removing at least a portion of the meniscus rather than restoration of the torn tissue.

Such treatment can result in permanent problems for the patient. Partial removal can lead to function loss. This, in turn, can contribute arthrosis in the knee joint.

Other known treatments often comprise substantial interventions. These are linked to risks and often result in a protracted and unpleasant rehabilitation period. In addition, the treatment's success is often inadequate. In some cases, there may be consequential damage. This can lead to pain that is not completely alleviated by the intervention. Additionally, it is quite possible for freedom-of-movement to never be completely restored. In many cases, additional intervention is necessary.

SUMMARY

The invention features the possibility of treating a ruptured body component of the type formed by hard connective tissue and doing so with low risk and a particularly short rehabilitation phase.

In one aspect, the invention features a fibrin adhesive be used during minimally-invasive treatment of a ruptured body component by adhesively bonding a ruptured body component. A suitable physiological adhesive is a fibrin adhesive.

As used herein, a "body component" will mean a body component formed from "hard connective tissue," which itself means supporting tissue, such as cartilage tissue and taut connective tissue. The term "connective tissue" particularly preferably comprises cartilage, and in particular, meniscus tissue. The term "taut connective tissue" includes, in particular, taut parallel-fiber connective tissue, and in particular tendons and/or ligaments.

In some practices, treatment includes locating the rupture, providing the fibrin adhesive, and supplying the fibrin adhesive at the ruptured body component.

In other practices, treatment includes locating the rupture in the ruptured body component, positioning a cannula having a first end for supplying a liquid from a reservoir in the cannula and a second end for discharging a liquid so that the second end is positioned adjacent to or in a sub-region of the rupture, providing the fibrin adhesive, and supplying the fibrin adhesive through the first end of the cannula and through the second end of the cannula.

It is preferable to diagnose the existence of a ruptured body component before the locating step. This can be performed by, for example, a clinical examination and/or an imaging diagnosis. The locating step typically includes locating a tear in the ruptured body component. This can be performed, for example, by an imaging method.

Examples of imaging methods include those based on x-ray radiation, such those that use computer tomography. Other examples include those methods that rely on magnetic resonance tomography, referred to herein as "MRT." The use of an imaging method that enables three-dimensional acquisition and display of data and therefore three-dimensional location of the rupture, in particular with regard to its location, shape, and/or extension, is preferred. The use of an MRT method is preferred in this case, because it avoids exposing the patient to ionizing radiation.

An alternative practice includes positioning a cannula that has a first end and a second end. The first end supplies liquid from a reservoir in the cannula. The second end discharges the liquid. The second end is therefore positioned adjacent to or in a sub-region of the rupture.

Proper positioning of the cannula permits the later step of supplying fibrin adhesive, by way of the cannula, directly at or in the rupture. This promotes adhesive bonding of the rupture.

In some practices, cannula positioning includes using an imaging method to monitor the cannula to ensure guiding fibrin adhesive to the rupture, thus promoting the most efficient adhesive bonding of the rupture.

When using MRT methods, it is preferable to use MRT-capable contrast agents. These increase contrast. Preferably, the contrast agents act quickly enough so that they change contrast within the relaxation times in the MRT method.

When using MRT, it is preferable to use MRT-compatible cannulas. Injection with contrast agent promotes correct positioning of such cannulas.

The next step is to provide the fibrin adhesive. In some practices, this includes removing a ready-to-use fibrin adhesive from a package. In other practices, this includes mixing components immediately before and during use.

The fibrin adhesive thus provided is then supplied to the ruptured body component, and in particular, to the tear. One way to do this is to inject the fibrin adhesive using a cannula.

Whichever way this is carried out, it is preferable that the fibrin adhesive completely fill up the tear. The fibrin adhesive is preferably supplied only to the tear. This will avoid undesired adhesive bonding of body components adjacent to the ruptured body component. Accurate location of the rupture or tear is a particularly useful way to avoid such unintended adhesion.

In those cases in which the fibrin adhesive is made on the spot from multiple components, it is useful to execute the foregoing steps jointly. This can be carried out using a cannula having multiple parallel channels that deliver the components to the rupture, where they can then mix to form the adhesive in situ.

Some practices include the use of a quick-curing fibrin adhesive. In such cases, it becomes possible for the now-bonded body component to bear weight again. In some cases, only a few seconds is required for the adhesive to set.

As an example, a patient who undergoes the foregoing treatment for a torn meniscus can often begin running again more or less immediately after treatment. This is possible because the foregoing method dispenses with the need to wait for healing or growth of the body component to restore its load-bearing capacity. The treated body component's load-bearing capacity returns upon curing of the fibrin adhesive. This can take only a few seconds depending on the fibrin adhesive used. Post-treatment rehabilitation is therefore substantially shortened using the described treatment method.

From the patient's viewpoint, the treatment method only requires a single injection. As used herein, such a small intervention is considered "minimally-invasive." Because the described treatment method is minimally-invasive, it can be carried out using only local anesthesia. Depending on the body component to be treated and depending on the type and extent of the rupture, anesthesia can sometimes be committed. In either case, it becomes possible to avoid or substantially reduce the risks of anesthesia.

Yet another advantage of the treatment method described herein is its high level of treatment success, as manifested by its low recurrence rates.

Fibrin adhesive is particularly well-suited for adhesively bonding a meniscus tear, such as a rupture of an inner or outer meniscus in the knee.

In a further preferred embodiment, the body component to be treated has a tear that is closable by at least partial filling using the fibrin adhesive. As used herein, "closing" a tear means using the fibrin adhesive to reconnect those parts of the body component that have been partially separated by the tear.

The treatment method as described herein is particularly suitable for treating a body component that has been partially or completely torn. In particular, the treatment method is suitable for treating a completely or partially torn meniscus, such as an inner and/or outer meniscus in the knee.

As used herein, "adhesive bonding" means that the tear is at least partially filled by the fibrin adhesive in such a way that the fibrin adhesive forms a mechanically loadable connection between tear surfaces.

As used herein, "tear surfaces" are surfaces that were formed as a result of separation caused by the tear.

Whether the tear is to be partially or completely filled, it is preferable that the fibrin adhesive be supplied to the ruptured body component, and in particular, directly into a part of the tear.

The treatment method described herein is particularly useful when either the tear surfaces are close to each other or when the tear does not twist sub-regions of the body component relative to each other. This means that the treatment can be carried out without having to move the tear surfaces towards each other and without having to pivot the tear surfaces relative to each other using a mechanical actuator.

The treatment can therefore be performed without the tear surfaces having to be moved toward one another and/or pivoted in relation to one another by mechanical action, for example.

In a further embodiment, the fibrin adhesive is provided in the form of a liquid solution and supplied to the body component to be treated via injection through a cannula.

In yet another embodiment, a solvent is admixed to the fibrin adhesive, for example to alter its viscosity, for example by increasing it. Alternatively, a solvent dissolves the fibrin adhesive. After treatment, as the fibrin adhesive cures, the body resorbs the solvent.

Having a higher viscosity can, in many cases, facilitate injection of the fibrin adhesive. For example, the fibrin adhesive will be able to penetrate particularly well into the tear and be distributed over the tear surfaces.

Some practices include the temporary visual display and location of the body component during the treatment.

In some practices, the rupture of the body component to be treated is first located, using, for example, an imaging method. In such embodiments, it is also possible to view the body component during delivery of the fibrin adhesive, for example while a cannula introduces the fibrin adhesive into the region to be treated. This promotes accurate delivery thereof.

The same imaging method is preferably, but not necessarily, used in other treatment steps. Suitable imaging methods include MRT (magnetic resonance tomography) and/or CT (computer tomography).

In the particular cases of treating a knee's meniscus, it is preferable to use MRT, and in particular, open magnetic resonance tomography. Such imaging includes generating a substantially constant magnetic field using a superconducting main coil and exposing the patient to that field. At the same time, an excitation coil generates a time-varying magnetic field at the knee. This permits display of the meniscus.

Open magnetic resonance tomography using an open main coil means that it is not necessary to enclose the patient's entire length. This is more comfortable for the patient and also permits greater access to the patient. In a preferred practices, the excitation coil is one that can be opened and closed around the patient's knee.

Some embodiments feature imaging the cannula used during injection. When MRT is used, the cannula is formed from a paramagnetic or diamagnetic material. In some practices, the cannula comprises titanium.

Because the surgeon is able to actually see the cannula, it becomes possible to precisely position the cannula and to monitor its position during the injection. This permits the cannula to be guided with great accuracy to the torn body component so that the tear can be adhesively bonded.

Furthermore, it is preferable for the fibrin adhesive to also be displayed by the imaging method. Therefore, it can be recognized by the imaging method whether and to what extent the tear is filled by the fibrin adhesive. The dosing of the fibrin adhesive is preferably performed on the basis of the imaging method.

In a further preferred embodiment, a marking is applied to the skin of a patient to be treated, which is used as a zero point of a coordinate system, wherein the injection of the fibrin adhesive is performed on the basis of the coordinate system.

The marking can take the form of a geometric body that is adhesively bonded to the patient's skin. In some practices, the geometric body has a size that is on the order of a few millimeters.

As a marking, some practices make use of a material that can be displayed by the imaging method. Some practices use a capsule or ball that is filled by a liquid that can be seen in an MRT image. A suitable liquid is one that includes fat, preferably in the form of an oil.

When displaying the data using the appropriate imaging method, the marking can thus be easily found and used as the zero point of the coordinate system. Thus, by way of a comparing the position of the marking on the body of the patient and the position of the marking in the image, it becomes easier to accurately align the cannula.

On the basis of the marking and the anatomy of the patient, for example, on the basis of the external contours of the body component, and also the position of the rupture in relation to the marking and in relation to the anatomy of the patient, on the basis of the visual display, a penetration point, a penetration angle, and a penetration depth for the cannula can be determined and the cannula can subsequently be introduced accordingly into the tissue of the body component.

The injection of the fibrin adhesive is preferably performed by a cannula that is guided by an automated injection device. The guiding of the injection needle can be performed by motors and/or actuators of the injection device.

Some practices control the injection device using the coordinate system and corresponding software. The coordinate system is only provided virtually in the software. In these practices, the marking is essentially an interface between the virtually existing coordinate system and reality. In the case of an MRT method, motors and/or actuators are preferably formed outside the significant scattering field, in particular outside the 10 gauss contour, and/or as magnetically encapsulated.

Automation, while useful, is by no means required. Some practices are carried out manually by carrying out a manual injection using a manually operated cannula with MRT monitoring.

In particular, a penetration point, a penetration depth, and a penetration angle can be defined using the imaging method and on the basis of the coordinate system. If an automated injection device is used, the values thus obtained for the penetration depth and the penetration angle can be transferred to the software of the injection device. This means that the cannula actually penetrates according to these values into the patient's body. Subsequently, the injection device guides the injection needle on the basis of these values and thus implements the values from the software accordingly.

If an automated injection device is not used, the values obtained from the imaging method and on the basis of the coordinate system for the penetration point, the penetration depth, and the penetration angle can be used manually by inserting the cannula a penetration point ascertained in accordance with the data of the imaging method in a corresponding penetration depth at the corresponding penetration angle. After having used the cannula, the positioning thereof with respect to the rupture can be checked again by the imaging method.

An alternative practice features applying plural markings to the patient's skin. This defines a zero point, or coordinate origin, and axes for a coordinate system.

In this practice, it is possible to compensate for patient movement. This permits delivering a particularly precise supply of the fibrin adhesive at the ruptured body component.

Further practices of the invention feature defining any one or more of the following during the injection: the cannula's penetration point, its penetration depth, and its penetration angle in three-dimensions.

Other practices feature, after having carried out the injection, holding the ruptured body component without movement for some predetermined time that depends on how fast the adhesive solidifies. A suitable time would be at least 30% greater than the fibrin adhesive's solidification time, or 50% greater than the fibrin adhesive's solidification time. As used herein, "solidification time" means the required for the fibrin adhesive to reach its final strength after having been applied.

Other practices include holding the body component still following application of fibrin adhesive until such time as the fibrin adhesive is cured or solidified. These practices include those in which the time spent holding the body component still is enough to completely cure the fibrin adhesive.

Alternative practices include mixing first and second components to make the fibrin adhesive. Among these practices are those in which the first component includes any one or more of human fibrinogen having a concentration in the range of 80 milligrams per milliliter to 100 milligrams per milliliter, aprotinin having a concentration in the range of 2800 kallidinogenase inactivator units per milliliter to 3200 kallidinogenase inactivator units per milliliter, and polysorbate 80 having a concentration in the range of 0.6 milligrams per milliliter to 1.9 milligrams per milliliter and those in which the second component includes any one or more of human thrombin having a concentration in the range of 400 international units per milliliter to 600 international units per milliliter, and calcium chloride having a concentration in the range of 35 micromoles per milliliter to 45 micromoles per milliliter. Such embodiments of fibrin adhesive are particularly suitable for the treatment of a ruptured body component which is formed by hard connective tissue.

A composition available under the trade name TISSEEL® is preferably useful as the fibrin adhesive. In such a case, the first component comprises human fibrinogen having a concentration of 91 milligrams per milliliter, aprotinin having a concentration of 3000 kallidinogenase inactivator units per milliliter, and polysorbate 80 having a concentration in the range of 0.6 milligrams per milliliter to 1.9 milligrams per milliliter, while the second component comprises human thrombin having a concentration of 600 international units per milliliter, and calcium chloride having a concentration of 40 micromoles per milliliter.

In some practices, the amount of fibrin adhesive used to treat the meniscus is between 1 and 4 milliliters. In other practices, the amount of fibrin adhesive used to treat the meniscus is between 1.5 and 3 milliliters. And in yet other practices, the amount of fibrin adhesive used to treat the meniscus is between 1.7 and 2.5 milliliters.

BRIEF DESCRIPTION OF THE DRAWING

The invention and the technical environment will be explained in greater detail hereafter on the basis of the FIGURE. The FIGURE shows a particularly preferred embodiment. However, the invention is not restricted to this illustrated embodiment. In particular, the FIGURE and in particular the illustrated size ratios are only schematic.

FIG. 1 shows a schematic illustration of the treatment of a rupture of a body component.

DETAILED DESCRIPTION

FIG. 1 shows a patient 1 in an open magnetic resonance tomograph 3 having an excitation coil 4 that is placed around the knee of the patient 1. The main coil of the tomograph 3 is omitted for clarity. In the example, shown the tomograph 3 displays a body component 2 to be treated. The body component 2 is one formed by hard connective tissue. In the illustrated example, the body component 2 is a meniscus 12.

A rupture of the meniscus 12 is treated in a minimally-invasive manner by adhesively bonding the meniscus 12 using a fibrin adhesive. To carry this out, the open magnetic resonance tomograph 3 is used for locating the meniscus 12. The fibrin adhesive is then supplied, for example, as a solution. A useful method for providing the solution is to inject the solution into the meniscus 12 using an injection device 13 having at least one cannula 5. A particularly precise injection of the fibrin adhesive can be carried out by a coordinate system 9 having a first axis 7 and a second axis 8 perpendicular to the first axis 7. A marking 10 on the patient's skin 11 indicates the coordinate origin 6 of the coordinate system 9.

A rupture of a body component 2, for example, a meniscus 12, can be treated particularly well by adhesive bonding using fibrin adhesive. The foregoing minimally-invasive intervention permits such treatment with particularly low risk and a particularly short rehabilitation phase.

Having described the invention, and a preferred embodiment thereof, what is claimed as new, and secured by Letters Patent is:

1. A method of minimally-invasive treatment of a patient's ruptured body component, the method comprising:
   treating the ruptured body component, said body component being a meniscus made of hard connective tissue, wherein treating said ruptured body component comprises:
      obtaining, from a magnetic resonance tomography (MRT) imaging system placed outside the patient's body, image data of the ruptured body component during all steps of the minimally-invasive treatment of the patient's body component;
      bonding a marking comprising a geometric body to the patient's skin, said marking being made of a material detectable by the MRT imaging system placed outside the patient's body;
      delivering through skin tissue of the patient an MRT-compatible cannula constructed from a paramagnetic or diamagnetic material that is seen by the MRT imaging system, wherein delivering the cannula comprises:
         computing from the obtained image data penetration data based on a location of the ruptured body component and a position of the cannula relative to the bonded marking as the cannula is guided towards the ruptured body component, wherein the penetration data includes at least a penetration point of the cannula, a penetration angle of the cannula, and a penetration depth of the cannula, and
         guiding the cannula based on the computed penetration data, the guiding includes injecting an MRT-compatible contrast agent through the guided cannula during the guiding to promote correct positioning of the guided cannula; and
      in response to determining, based on the obtained image data, that the guided cannula is at a location near or into the ruptured body component, injecting a fibrin adhesive for adhesively bonding with the ruptured body component, the fibrin adhesive being injected through the same MRT-compatible cannula, through which the MRT-compatible contrast agent was injected during the guiding of the cannula, after the guided cannula is determined to reach the location near or into the ruptured body component; and
   wherein the method further comprises guiding the cannula to the ruptured body component using an automatic guidance system fitted with the cannula, the automatic guidance system being actuated based on data generated according to the MRT imaging system.

2. The method of claim 1, further comprising partially filling a tear in said ruptured body component with said fibrin adhesive.

3. The method of claim 1, further comprising obtaining said fibrin adhesive by mixing together a first component and a second component, wherein said first component comprises human fibrinogen at a concentration in the range of 80 mg/ml to 100 mg/ml, aprotinin at a concentration in the range of 2800 kallidinogenase inactivator units (KIE)/ml to 3200 KIE/ml, and polysorbate 80 at a concentration in the range of 0.6 mg/ml to 1.9 mg/ml, and wherein said second component comprises human thrombin at a concentration in the range of 400 international units (I.E.)/ml to 600 I.E./ml, and calcium chloride at a concentration in the range of 35 μmol/ml to 45 μmol/ml.

4. The method of claim 3, further comprising providing said fibrin adhesive as a liquid and injecting said liquid into said ruptured body component using the MRT-compatible cannula.

5. The method of claim 4, further comprising applying the marking to said patient's skin, said marking serving as a zero point of a coordinate system, and injecting said fibrin adhesive is performed on the basis of said coordinate system.

6. The method of claim 5, further comprising defining a factor on the basis of said coordinate system, said factor being selected from the group consisting of the penetration depth of said MRT-compatible cannula, and the penetration point of said cannula.

7. The method of claim 5, further comprising defining a factor on the basis of said coordinate system, said factor being a three-dimensional penetration angle of said cannula used for the injection.

8. The method of claim 7, further comprising rendering said body component immovable for a predetermined duration following injection of said fibrin adhesive.

9. The method of claim 8, further comprising using between 1 milliliter and four milliliters of said fibrin adhesive to treat said damaged meniscus.

10. The method of claim 1, wherein delivering the paramagnetic or the diamagnetic material cannula comprises inserting the paramagnetic or diamagnetic material cannula at a single penetration point on the skin tissue of the patient.

11. The method of claim 1, wherein guiding the cannula to the ruptured body component using the automatic guidance system comprises determining, based on image data from the MRT imaging system, one or more of the penetration point, the penetration depth, or the penetration angle to automatically penetrate and guide the cannula.

12. The method of claim 1, wherein guiding the cannula to the ruptured body component comprises guiding the cannula according to the imaging generated, based in part on the MRT-capable contrast agent included with the fibrin adhesive contained within the MRT-compatible cannula, by the MRT imaging system.

13. The method of claim 1, wherein delivering the MRT-compatible cannula comprises:
   determining the penetration point, the penetration angle, and the penetration depth for inserting the MRT-compatible cannula to deliver the fibrin adhesive to the ruptured body component based on the location of the ruptured body component and the position relative to the bonded marking comprising the geometric body determined from the imaging data;
   penetrating the body of the patient with the cannula at the determined penetration point; and
   displacing the cannula towards the ruptured body component at the determined penetration angle.

14. The method of claim 13, wherein injecting the fibrin adhesive comprises injecting the fibrin adhesive by an automated injection device.

15. The method of claim 1, wherein bonding the marking comprises bonding to the patient's skin a liquid-filled ball or capsule geometric body that is visually detectable by the MRT-imaging system.

* * * * *